(12) United States Patent
Rioux et al.

(10) Patent No.: US 7,174,217 B2
(45) Date of Patent: **\*Feb. 6, 2007**

(54) APPARATUS AND METHODS FOR ASSISTING ABLATION OF TISSUE USING MAGNETIC BEADS

(75) Inventors: Robert F. Rioux, Ashland, MA (US); Robert Garabedian, Tyngsboro, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/224,864

(22) Filed: Sep. 12, 2005

(65) Prior Publication Data

US 2006/0015098 A1 Jan. 19, 2006

Related U.S. Application Data (63) Continuation of application No. 10/665,110, filed on Sep. 16, 2003, now Pat. No. 6,961,620.

(51) Int. Cl.
*A61F 7/00* (2006.01)
(52) U.S. Cl. .......................................... 607/99; 600/9
(58) Field of Classification Search .............. 600/9–15; 128/897–899; 607/1, 3, 96, 98, 99, 100, 607/101, 115; 604/506–508
See application file for complete search history.

(56) References Cited

U.S. PATENT DOCUMENTS 4,945,912 A   8/1990   Langberg 5,921,244 A   7/1999   Chen et al.
6,148,236 A   11/2000  Dann (Continued)

FOREIGN PATENT DOCUMENTS

WO   WO 03/084593   10/2003

OTHER PUBLICATIONS

Moroz et al, "Magnetically Mediated Hyperthermia: Current Status and Future Directions", International Journal of Hyperthermia, Basingstoke, GB. vol. 18, No. 4, Jul. 2002, pp. 267-284.

(Continued)

*Primary Examiner*—John P. Lacyk
(74) *Attorney, Agent, or Firm*—Vista IP Law Group LLP (57) ABSTRACT

A system for treating tissue includes a source of conductive and/or magnetic beads, a first member, e.g., a catheter or cannula, coupled to the source of magnetic beads, and a second member, e.g., a catheter or cannula, carrying a magnet on its distal end. The system is used for ablating or otherwise treating tissue within a target tissue region including a blood vessel contacting or passing therethrough. Magnetic beads are introduced into the target tissue region, e.g., using the first member, and a magnetic field is generated within the target tissue region, e.g., using the second member, to cause the magnetic beads to migrate towards a wall of the vessel. Energy is delivered into the target tissue region, e.g., to heat tissue therein, and the magnetic beads may attenuate or enhance treatment of tissue adjacent to the vessel.

27 Claims, 4 Drawing Sheets

U.S. PATENT DOCUMENTS 6,296,604 B1    10/2001    Garibaldi et al.
6,423,056 B1    7/2002    Ishikawa et al.
6,540,657 B2    4/2003    Cross, III et al.
6,961,620 B2 *    11/2005    Rioux et al. .................. 607/99
2002/0087177 A1    7/2002    Wallace et al.
2003/0114727 A1    6/2003    Wallace

OTHER PUBLICATIONS

PCT International Search Report for PCT/US2004/028715, Applicant: Scimed Life Systems, Inc., Forms PCT/ISA/210 and 220, dated Dec. 6, 2004 (7 pages).

PCT Written Opinion of the International Search Authority for PCT/US2004/028715, Applicant: Scimed Life Systems, Inc., Form PCT/ISA/237, dated Dec. 6, 2004 (4 pages).

* cited by examiner

APPARATUS AND METHODS FOR ASSISTING ABLATION OF TISSUE USING MAGNETIC BEADS

This application is a continuation of U.S. application Ser. No. 10/665,110, filed on Sep. 16, 2003, now U.S. Pat. No. 6,961,620, the disclosure of which is expressly incorporated herein by reference.

FIELD OF THE INVENTION

The present invention relates generally to apparatus and methods for treating tissue within a patient, and, more particularly, to apparatus and methods for delivering beads into tissue to enhance treating the tissue, and to apparatus and methods for assisting treating tissue using conductive and/or magnetic beads, e.g., during an ablation procedure.

BACKGROUND

Electrosurgical instruments for delivering radio frequency (RF) electrical energy into tissue are known. For example, U.S. Pat. No. 5,868,740 discloses electrosurgical probes that include a plurality of wire electrodes that may be advanced into tissue from the distal end of a cannula. The electrodes may be energized with RF energy in a monopolar or bipolar mode to heat and/or necrose a target tissue region. Such probes have been suggested for treating tumors within organs, such as the liver, kidney, pancreas, stomach, lungs, and spleen.

One concern with RF ablation is the "heat sink" effect, which may occur because of the vascular nature of the tissue being treated. For example, within the liver, RF energy may be delivered to heat and necrose a tumor. If the tumor is located near a large vessel, blood passing through the vessel may conduct heat away from the tumor. This may cause the heat to be distributed unevenly, possibly resulting in tumor cells adjacent to the vessel not being sufficiently heated and/or destroyed. To ensure that the cells nearer to the vessel are sufficiently heated, additional energy may be applied to the tumor, but this may expand the heated region into tissue located away from the vessels, which may risk damaging healthy tissue adjacent to the tumor.

Accordingly, apparatus and methods for facilitating heating or otherwise treating tissue would be useful.

SUMMARY OF THE INVENTION

The present invention is directed to apparatus and methods for treating tissue within a patient, and, more particularly, to apparatus and methods for delivering particles or beads into tissue to enhance treating the tissue, and to apparatus and methods for assisting ablating or otherwise treating tissue, e.g., with thermal energy and/or therapeutic agents, using conductive and/or magnetic beads.

In accordance with a first aspect of the present invention, a system is provided for treating tissue within a target tissue region that includes a source of conductive and/or magnetic beads for delivering the beads into the target tissue region, a first elongate member including a proximal end, a distal end configured for introduction into the target tissue region, and a magnet carried by the distal end, the magnet configured for inducing a magnetic field within the target tissue region to cause the beads within the target tissue region to migrate in a desired manner.

In addition or alternatively, the first elongate member may be a flexible or semi-rigid catheter insertable into a vessel contacting or passing through the target tissue region. In a further alternative, the first elongate member may be a substantially rigid, semi-rigid, or flexible cannula that may be introduced into the target tissue region.

In accordance with another aspect of the present invention, a method is provided for treating tissue within a target tissue region. Magnetic and/or conductive beads may be introduced into the target tissue region, and a magnetic field may be generated within the target tissue region to cause migration of the beads. Energy may be delivered to treat tissue within the target tissue region, the beads enhancing treatment of the tissue.

In one embodiment, the beads may be introduced into the target tissue region by introducing a cannula into the target tissue region, the beads being delivered into the target tissue region from the cannula. In another embodiment, the beads may be introduced into the target tissue region by introducing a catheter into a vessel contacting or passing through the target tissue region, the beads being delivered into the target tissue region from the catheter.

The magnetic field may be generated by introducing an elongate member into the target tissue region, the elongate member carrying a magnet thereon. For example, the elongate member may be a catheter introduced through a vessel contacting or passing through the target tissue region, the catheter being manipulated to place the magnet at a desired position within the target tissue region. Alternatively, the elongate member may be a substantially rigid member that is introduced directly into the tissue of the target tissue region. In a preferred embodiment, the beads are caused to migrate towards a vessel contacting or passing through the target tissue region to enhance delivery of energy to tissue adjacent the vessel.

Optionally, energy may be delivered by introducing one or more electrodes into the target tissue region, and delivering electrical energy to the target tissue region via the one or more electrodes. For example, the one or more electrodes may be carried by a needle probe including one or more needles that may be inserted into the target tissue region.

In accordance with another aspect of the present invention, a method is provided for ablating tissue within a target tissue region, the target tissue region including a blood vessel contacting or passing through the target tissue region. Magnetic and/or conductive beads may be introduced into the target tissue region. Optionally, a magnetic field may be generated within the target tissue region to cause the beads to migrate in a desired manner, e.g., towards a wall of the vessel. Energy may be delivered into the target tissue region to heat tissue therein, the beads enhancing heating of tissue adjacent to the vessel.

In one embodiment, the beads maybe introduced into the vessel, and the magnetic field may cause the beads to migrate against an inner surface of the wall of the vessel. Alternatively, a magnet may be introduced into another vessel contacting or passing through the target tissue region to generate the magnetic field.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals, and in which.

DETAILED DESCRIPTION OF THE ILLUSTRATED EMBODIMENTS

Figure 1:
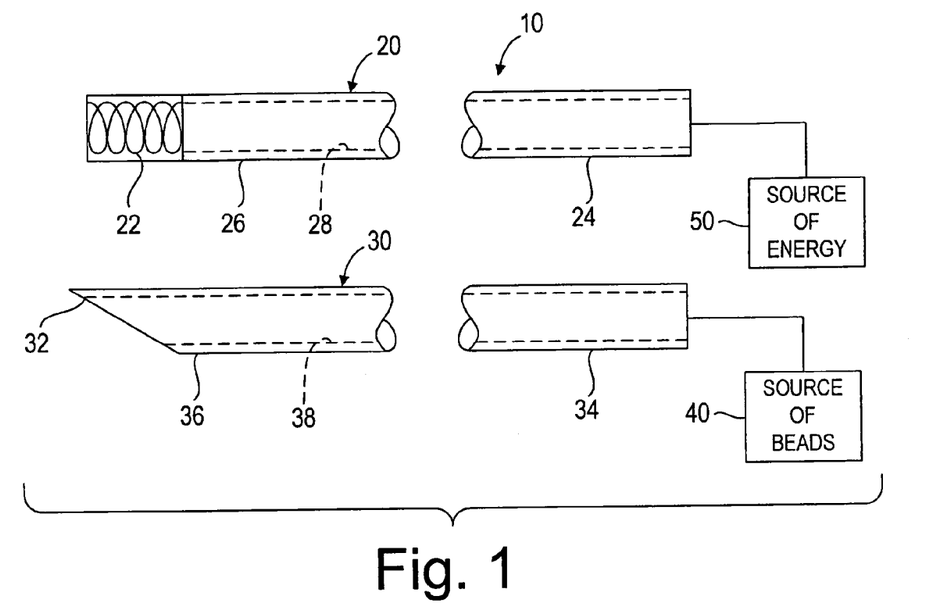
FIG. 1 is a side view of an embodiment of a system for treating tissue using magnetic beads to enhance ablation using electrical energy, in accordance with the present invention.

Turning to the drawings, in which similar or corresponding parts are identified with the same reference numeral, FIG. 1 shows a preferred embodiment of an ablation system 10 that includes a first member 20 carrying a magnet 22, and a second member 30 coupled to a source of magnetic beads 40 for delivering magnetic beads into a patient's body, in accordance with the present invention. Alternatively, a single member, e.g., a catheter or cannula including a magnet and coupled to a source of magnetic beads (not shown), may be provided for introducing magnetic beads and for generating magnetic fields within a patient's body.

The first member 20 may be a catheter or other elongate member including a proximal end 24 and a distal end 26 having a size and shape to facilitate insertion into a patient's body (not shown). Optionally, the first member or catheter 20 may include a lumen 28 extending between the proximal and distal ends 24, 26, e.g., for advancing the catheter 20 over a guidewire or other rail (not shown) and/or for introducing fluid therethrough. One or more leads, e.g., wires or other conductive paths (not shown), may extend from the magnet 22 towards the proximal end 24 of the catheter 20.

The catheter 20 may be formed from conventional materials, e.g., metal, plastic, and the like. In one embodiment, the catheter 20 may increase in flexibility from the proximal end 24 to the distal end 26. For example, a distal portion of the catheter 20 may be substantially flexible and soft (e.g., a "floppy" catheter) to facilitate advancement into and/or manipulation within tortuous anatomy. A proximal portion of the catheter 20 may be semi-rigid or substantially rigid, e.g., to facilitate pushing the catheter 20 without buckling or kinking. In other embodiments, the catheter 20 may have other variations in flexibility along its length, depending on a particular application. Alternatively, the first member 20 may be a substantially rigid probe, e.g., a needle with a sharpened distal tip and a magnet on or adjacent the distal tip (not shown) or a blunt tipped cannula carrying a magnet (also not shown). Exemplary embodiments of catheters that may be used are disclosed in U.S. Pat. No. 6,540,657, the disclosure of which is expressly incorporated by reference herein.

The proximal end 24 of the first member 20 may include one or more connectors (not shown) for connecting to other components of the system 10. For example, if the magnet 22 is an electromagnet, the proximal end 24 may include an electrical connector for coupling the magnet 22 to a source of energy 50, e.g., an electrical generator and/or battery, as described further below. In addition, the proximal end 24 may include one or more elements, e.g., a luer lock connector for connecting a source of fluid, e.g., saline or contrast (not shown), to the first member 20, or one or more ports for introducing a guide wire or other rail through the lumen 28, as is known in the art.

The second member 30 may be a cannula or catheter including a proximal end 34, a distal end 36, and a lumen 38 extending between the proximal and distal ends 34, 36. The second member 30 may be a substantially rigid needle having a sharpened distal tip 32, as shown in FIG. 1, such as a twenty two gauge (22 ga.) needle. Alternatively, the second member 30 may be a substantially rigid, semi-rigid, or flexible cannula or catheter that may be advanced through an introducer (not shown). In a further alternative, the second member 30 may be a catheter, e.g., between about three and five French (1–1.67 mm), constructed similar to the catheter described above (but without the magnet), that may be sufficiently flexible for advancement through a patient's vasculature.

The proximal end 34 may include a luer lock connector and the like (not shown) for connecting the source of magnetic beads 40 to the second member 30 such that magnetic beads may be delivered through the lumen 28. The distal end 36 may include a single outlet, as shown in FIG. 1, or may include a plurality of openings (not shown) for delivering the magnetic beads in a desired pattern.

In one embodiment, the beads provided from the source 40 may be spheres or particles having cross-sectional dimensions, e.g., diameters, between about ten nanometers (10 nm) and about twelve hundred microns (1200 μm), and preferably between about one and forty microns (1–40 μm). The beads, however, may also have other cross-sectional dimensions, as long as they are capable of migrating within a body. In addition, the beads may have other geometric shapes besides spherical shapes. The beads may be made from a biocompatible material that is highly conductive to heat, such as one or more metals, e.g., gold and/or ferric materials. Preferably, the beads are also magnetic. As used herein, "magnetic" refers to any material or composition that is capable of being magnetized or that is capable of being attracted to or repelled by a magnet.

In addition or alternatively, the beads may be coated with therapeutic or diagnostic compounds, e.g., on an outer surface of the beads. In addition or alternatively, the beads may be impregnated with such compounds. For example, the beads may be porous or may at least partially dissolve within the body to deliver compounds therein. The compounds carried by the beads may include chemotherapeutic agents that may enhance necrosis or other treatment of tissue. In addition or alternatively, the beads may carry a polyvinyl alcohol (PVA) particle, which may be used to absorb a drug. In yet a further alternative embodiment, the beads may include microparticles secured thereto that may be released from the beads when exposed to a magnetic field or other energy. Exemplary microparticles that may be used are available from FeRx Incorporated, San Diego, Calif.

In one embodiment, the beads may include circuits and/or switches configured for generating and/or regulating an amount of heat in response to a signal, e.g., radio frequency signals, received from an external control system or transmitter (not shown). An example of such beads is disclosed in U.S. Pat. No. 6,423,056 B1, the disclosure of which is expressly incorporated by reference herein. In an alternative embodiment, the beads may include nano-particles tuned to absorb or scatter light at desired wavelengths, including ranges where human tissue is relatively transparent. For example, an infrared laser may be positioned outside a body and used to irradiate the nano-particles, thereby causing them to deliver heat sufficient to heat, ablate, or otherwise treat tissue. Nano-particles are commercially available from Nanospectra Biosciences, Inc., Houston, Tex. In yet a further alternative embodiment, the beads may generate heat in response to a magnetic field, such as those disclosed in U.S. Pat. No. 6,149,576, the disclosure of which is expressly incorporated by reference herein.

The first and second members 20, 30 may have a length between about ten centimeters and about one hundred eighty centimeters (10–180 cm), and/or an outer diameter or cross-section between about three and eight French (3–8 FR) (i.e., between about 1–2.7 mm). However, the first and second members 20, 30 may also have other lengths and outer cross sectional dimensions suitable for a particular application.

Figure 2:
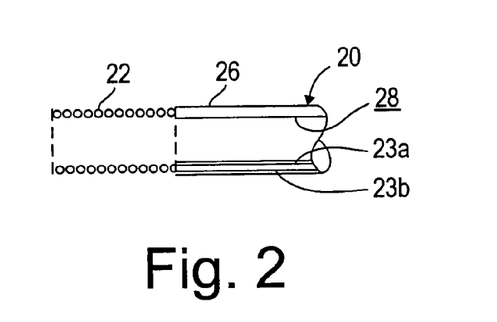
FIGS. 2–4 are cross-sectional views of alternative embodiments of a distal portion of a catheter illustrated in FIG. 1.

Turning to FIG. 2, the magnet 22 on the distal end 26 of the first member or catheter 20 may be a coiled solenoid or induction electromagnet. Alternatively, the distal end 26 of the catheter 20 may carry a permanent magnet (not shown) instead of an electromagnet 22. The magnet 22 may be connected to the distal end 26 of the catheter 20 such that the magnet 22 is at least partially exposed or uncovered. For example, the magnet 22 may be secured to the distal end 26 by welding, brazing, gluing, other suitable adhesive, and the like, depending on the materials from which the electromagnet 22 and the distal end 26 are made. As shown in FIG. 2, if the magnet 22 is an electromagnet, one or more leads 23 may extend from the magnet 22 towards the proximal end 24 of the catheter 20, e.g., for coupling to the source of energy 50 (not shown, see FIG. 1). Optionally, the catheter 20 may include a sensor, such as a temperature sensor and/or a magnetic field sensor (not shown) carried by the distal end 26.

Electrical current may be supplied to the magnet 22 by the source of energy 50 via lead wire 23a and returned by return wire 23b to induce a first magnetic field. Polarity through the magnet 22 may be reversed to induce a second magnetic field in an opposite direction from the first magnetic field. The magnet 22 may be configured for generating a sufficient magnetic field to mobilize or otherwise manipulate magnetic beads, such as those described above. The magnet 22 may generate higher magnetic fields for heavier beads, beads disposed in dense or viscous fluid, and/or beads that are further away from the magnet 22.

The strength of the magnetic field generated by the magnet 22 may depend upon a number of factors, such as the geometry of the magnet 22, the material from which the magnet 22 is made, and/or the amount of power supplied to the magnet 22 by the source of energy 50. In one embodiment, the power delivered to the magnet 22 from the source of energy 50 is adjustable. In this case, during use, the power may be incrementally increased until a desired magnetic field intensity is achieved. Alternatively, the power delivered to the magnet 22 may be fixed at a set level when activated. In this case, the source of energy 50 may deliver sufficient power to mobilize the beads within a prescribed distance from the magnet 22.

In another embodiment, the magnet 22 may be an adjustable electromagnet that may be configured for varying the intensity of the magnetic field. For example, the catheter 20 may include a core wire or other element (not shown) having a distal end (also not shown) secured to the distal end of the magnet 22. For example, the core wire may be disposed in the lumen 28 or within another lumen (not shown) within the catheter 20. The core wire may be advanced distally, thereby increasing the spacing between the pitches of the coils of the magnet 22 and increasing the intensity of the magnetic field, and retracted proximally to increase the intensity of the magnetic field.

In a further alternative embodiment, the magnet 22 may include two or more portions with each portion electrically isolated from the other portion(s). Each of the portions may be electrically connected to the source of energy 50, and may be individually or collectively activated to generate a magnetic field. If a weak magnetic field is desired, then only one of the portions may be activated. If a relatively stronger magnetic field is desired, then one or more additional portions may be activated.

Figure 3:
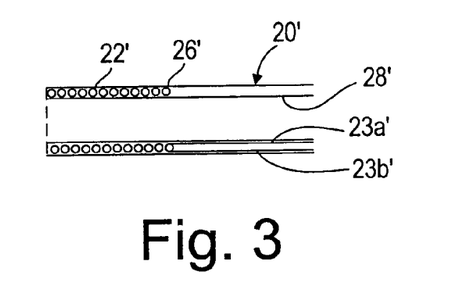
Figure 4:
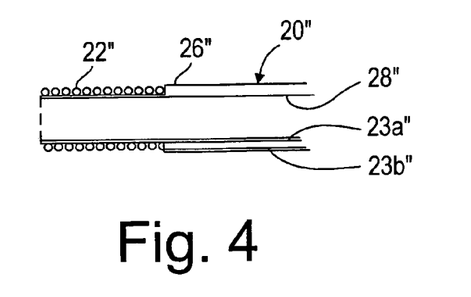

It should be noted that the manner in which the magnet 22 is secured to the distal end 26 and/or the configuration of the magnet 22 relative to the distal end 26 should not be limited to that shown in FIG. 2. For example, turning to FIG. 3, another embodiment of a catheter 20' is shown that includes a magnet 22' that is located at least partially within a wall of the catheter 20' at or adjacent to its distal end 26,' and preferably completely embedded in the wall of the catheter 20.' In a further alternative, shown in FIG. 4, the distal end 26" of the catheter 20" may include a recessed portion that carries a magnet 22" thereon.

Figure 5A:
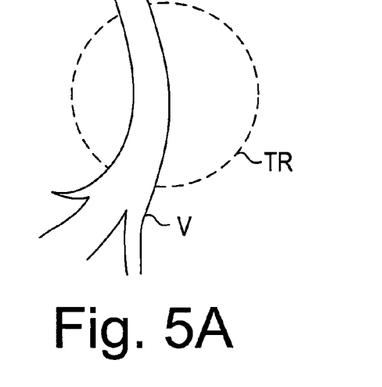
FIGS. 5A–5E are cross-sectional views, showing a method for using magnetic beads to enhance ablation of tissue, in accordance with the present invention.

Turning now to FIGS. 5A–5E, a method is shown for treating a target treatment region TR within tissue, such as a cancerous or benign tumor within a liver, using an ablation system, such as that shown in FIG. 1 and described above. It will be appreciated that the apparatus and methods described herein may be used to treat other conditions and/or tissues in other organs, tissue structures, or parts of a body, e.g., a pancreas, kidney, lung, and the like. First, FIG. 5A shows the treatment region TR before treatment, the treatment region TR having a vessel V, e.g., an artery and the like, passing through a portion of the treatment region TR. It will be appreciated that the vessel V need not pass entirely through the treatment region TR, but may extend along or adjacent to the treatment region TR such that blood flow through the vessel V may cause a heat sink for energy delivered to tissue within the treatment region TR.

Figure 5B:
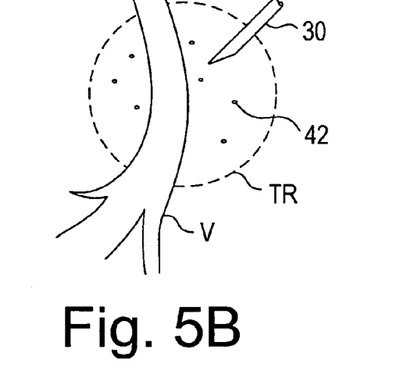

Turning to FIG. 5B, beads 42 may be delivered into the tissue within the treatment region TR. The beads 42 may be placed in a solution or otherwise suspended in a fluid, such as a saline solution or a contrast agent to ease delivery, and a bolus of the solution may be injected into the treatment region TR using a cannula or needle 30. As the beads 42 are injected, they may migrate and scatter randomly and/or substantially uniformly in the treatment region TR.

In one embodiment, a sharpened, hollow needle 30 may be inserted directly into the treatment region TR, e.g., percutaneously through the patient's skin (not shown). Alternatively, the surface of the organ or tissue surrounding the treatment region TR may be at least partially exposed surgically, as is well known to those skilled in the art. In a further alternative, an introducer (not shown) may be inserted into the treatment region TR, e.g., using an internal stylet (also not shown), as is known in the art. A blunt cannula (also not shown) may then be inserted through the introducer into the treatment region TR after the stylet has been removed. The introducer may be removed or may remain around the cannula as the beads 42 are delivered. Once the beads 42 are delivered, the delivery device, i.e., needle 30, cannula, or catheter, may be removed from the patient or may remain to allow additional beads to be delivered during the procedure.

Figure 5C:
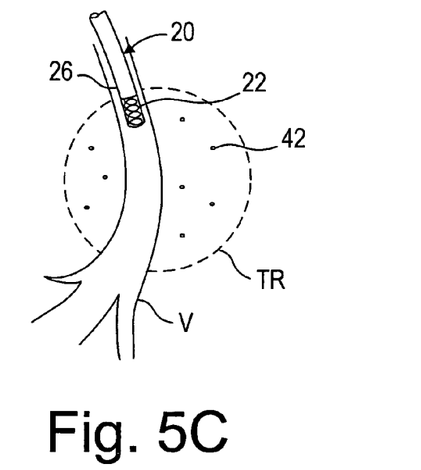

Turning to FIG. 5C, a catheter 20, such as that shown in FIG. 1 and described above including a magnet 22 on its distal end 26, may be advanced through the patient's vasculature until the distal end 26 enters the vessel V within the treatment region TR. For example, if the treatment region TR is located within a liver, the catheter 20 may be introduced percutaneously, e.g., into the femoral or other peripheral artery, and advanced into the hepatic artery, and into any branches necessary to reach the vessel V, as will be appreciated by those skilled in the art. The distal end 26 of the catheter 20 may be monitored during advancement using external imaging, e.g., fluoroscopy and the like, and the catheter 20 may include one or more radiopaque markers (not shown) to facilitate such imaging.

Figure 5D:
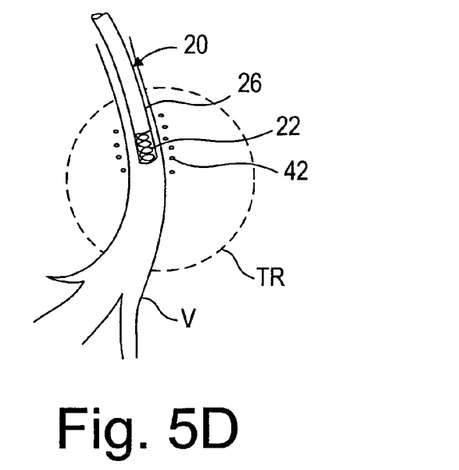
Figure 5E:
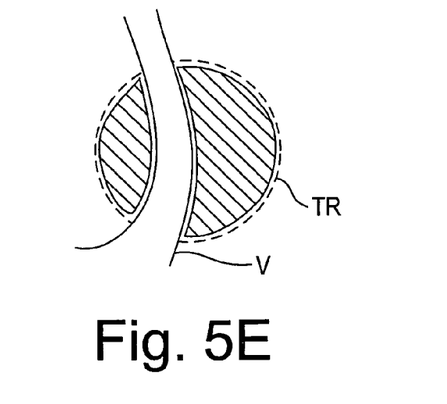

Turning to FIG. 5D, once the distal end 26 of the catheter 20 is properly positioned within the vessel V, the magnet 22 may be activated to generate a magnetic field within the treatment region TR. The magnetic field may cause the beads 42 to migrate within the treatment region TR in a desired manner. Preferably, the beads 42 migrate towards the wall of the vessel V due to their attraction to the magnet 22, thereby arranging the beads 42 around the vessel V. The intensity of the magnetic field may be fixed or may be adjusted to promote sufficient migration of the beads 42 within the treatment region TR, e.g., using the apparatus and methods described above. The migration of the beads 42 may be limited by the wall of the vessel V or by tissue immediately adjacent the wall of the vessel V such that the beads 42 to not pass through the wall of the vessel V.

Energy may then be delivered into the treatment region TR to heat, necrose, and/or otherwise treat tissue within the treatment region TR. For example, one or more electrodes (not shown) may be introduced into the treatment region TR, and electrical energy may be delivered from the electrode(s) to heat the tissue. Preferably, an array of needle electrodes (not shown) is inserted into the treatment region TR, as is disclosed in U.S. Pat. No. 5,868,740, the disclosure of which is expressly incorporated herein by reference. Alternatively, the device used to deliver the beads may include one or more electrodes, e.g., on an outer surface of the delivery device and/or deployable from the delivery device (not shown). Thus, electrical energy or other energy may be delivered to the treatment region TR using the same device that delivers the beads 42.

Without the beads 42, thermal energy generated within the treatment region TR (e.g., due to the delivered electrical energy) may be at least partially conducted away due to blood flow within the vessel V, which may result in an incomplete and/or irregular volume of tissue being necrosed. With the beads 42 surrounding the vessel V, however, the flow of electrical energy within the treatment region TR may be attenuated to enhance energy delivery to the tissue surrounding the vessel V. Stated differently, because of their conductive nature, the beads 42 may enhance delivering thermal energy to the tissue surrounding the vessel V as compared to the tissue within the treatment region TR located away from the vessel V. This enhanced thermal energy may at least partially, and, preferably, substantially, compensate for any energy loss due to the heat sink effect of the vessel V. Thus, the beads 42 may promote a more uniform heat distribution within the treatment region TR, thereby ensuring that the tissue within the treatment region TR is sufficiently heated. Consequently, the risk of live tumor cells remaining after an ablation procedure, particularly in the region closest to the vessel V, may be substantially reduced.

Once sufficient energy is delivered, the magnet 22 may be deactivated (if it is an electromagnet), and the catheter 20 may be removed from the patient's body using conventional methods. The electrode(s) or other devices used to deliver energy to the treatment region TR may also be removed. The beads 42 may be removed from the treatment region TR or may remain within the patient's body, e.g., indefinitely or until they metabolize if they are bioabsorbable.

In alternative embodiments, different types of beads and/or other sources of energy may be used to treat the treatment region TR. For example, the beads 42 may be activatable by a source of energy to generate heat in the tissue surrounding the vessel V. The source of energy may be an infrared generator, a magnetic field generator, or a RF generator, depending upon whether the beads 42 are infrared activated, magnetic field activated, or RF activated, respectively, as discussed previously. The source of energy may be positioned outside or inside the patient's body. The energy-activated beads may be used in conjunction with electrical energy delivery, or may be used before, after, and/or instead of electrical energy delivery.

In one embodiment, a catheter, similar to that shown in FIG. 1 and described above, may be provided with one or more element(s) (not shown) on its distal end that may be coupled to a source of energy (not shown) for activating the beads 42. For example, the element(s) may be one or more electrodes for delivering electrical energy, fiber optic elements for delivering laser or other light, or magnets. The distal end of the catheter may be inserted into the vessel V, similar to the methods discussed previously, and the source of energy may then transmit energy via the element(s) to the beads 42, causing the beads 42 to generate heat to enhance ablation of the tissue.

Returning to FIG. 5D, various techniques may be employed to assist migration of the beads towards the vessel V. For example, with the magnet 22 activated, the distal end 26 of the catheter 20 may be moved distally and/or proximally within the vessel V to cause the beads 42 to migrate along the vessel V as electrical energy is delivered to the treatment region TR. If the beads 42 are themselves magnets rather than merely being magnetic, the migration of the beads 42 may be reversed, e.g., away from the vessel V, by changing the polarity of the electromagnet 22.

When the beads 42 have been caused to migrate by the catheter 20 to desired locations, a source of energy may deliver energy to cause the beads 42 to generate heat or attenuate energy delivery to tissue adjacent or against the wall of the vessel V, as explained above. When desired lesions adjacent the wall of the vessel V have been created, the beads 42 may be deactivated, and the catheter 20 may be removed from the treatment region TR, also as described above. If it is desired to treat tissue at one or more additional site(s) adjacent the vessel V within the treatment region TR, the distal end 26 of the catheter 20 may be moved to another location with the magnet 22 activated, thereby "pulling" the beads 42 to another location adjacent the vessel V within the treatment region TR.

If the beads 42 are activatable, the beads 42 may be deactivated before they are caused to migrate to a new location, and then reactivated when they are at the new location. Alternatively, the beads 42 may remain activated (i.e., continue to generate heat) while the catheter 20 pulls them to a new location. This has the benefit of treating a substantially continuous region of tissue along and adjacent the wall of the vessel V to ablate or otherwise enhance treatment near the vessel V.

Figure 6:
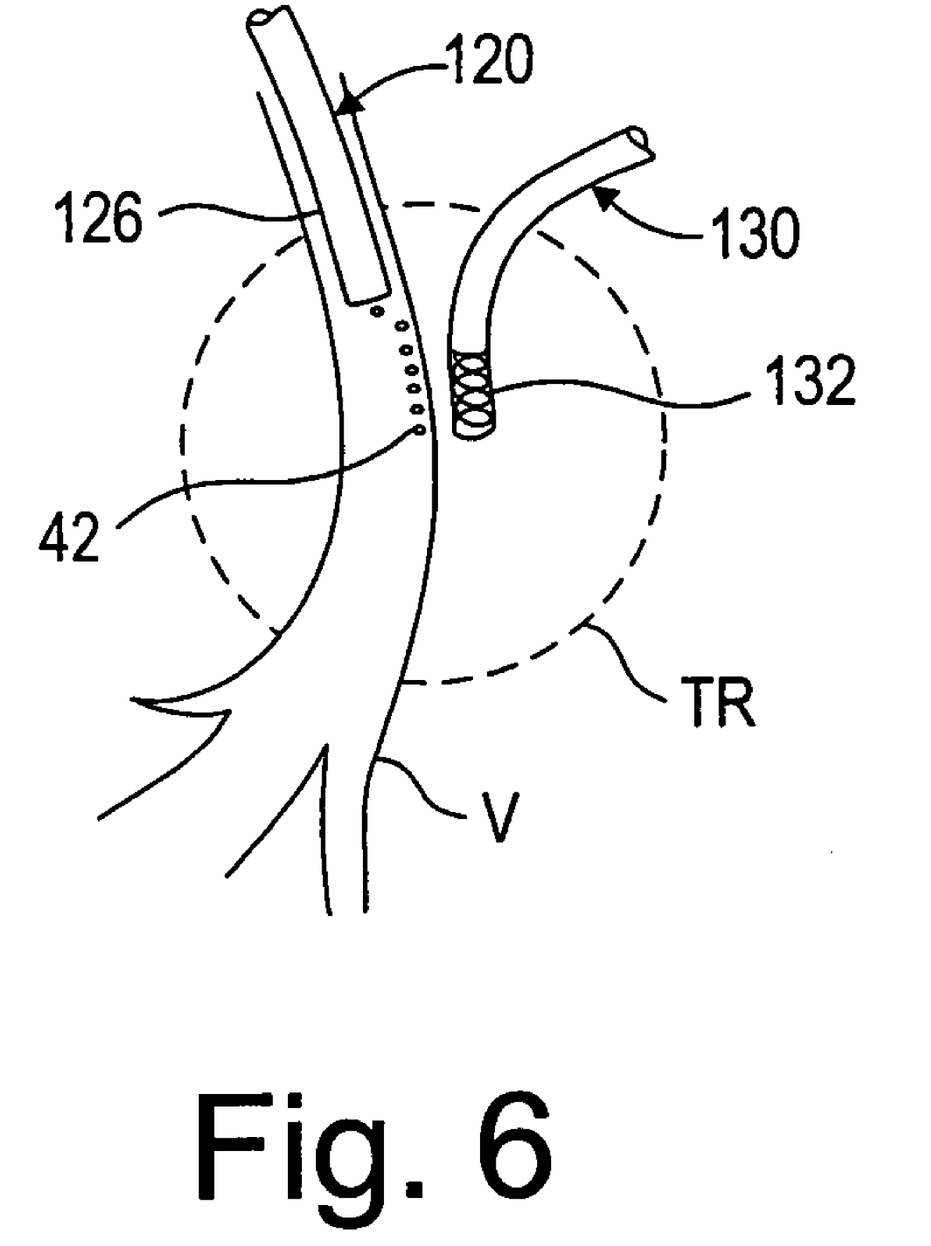
FIG. 6 is a cross-sectional view, showing an alternative method for using magnetic beads to enhance ablation of tissue, in accordance with the present invention.
Figure 7:
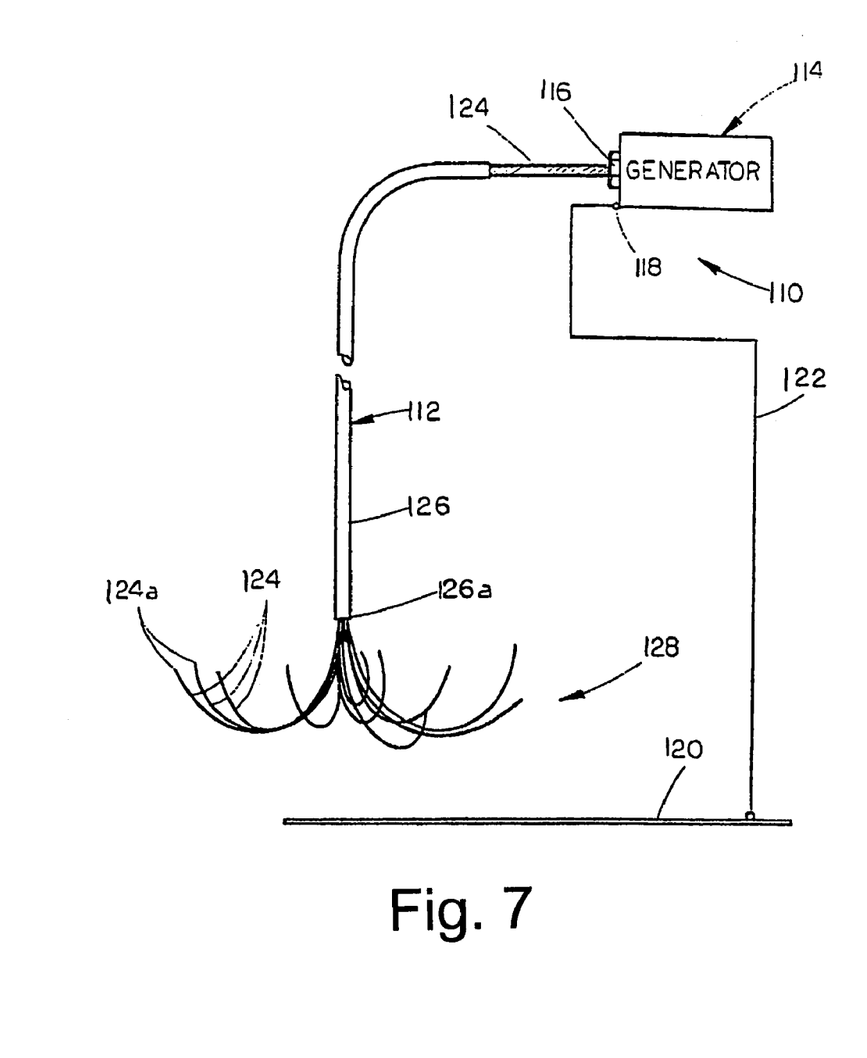
FIG. 7 is a side elevational view of a tissue ablation apparatus.
Figure 8:
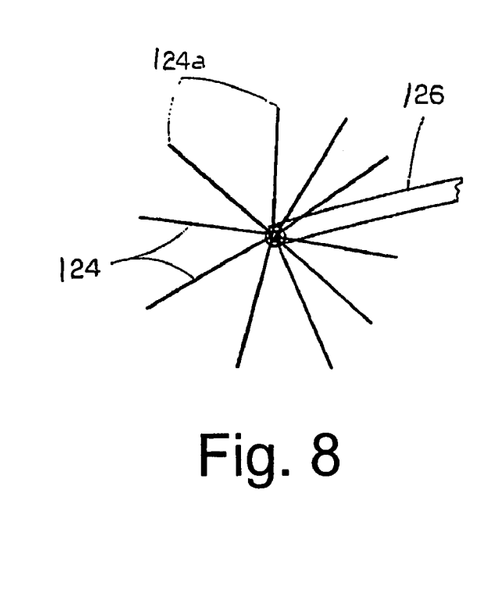
FIG. 8 is an end view of the apparatus of FIG. 7.

Turning to FIG. 6, another method is shown for treating a treatment region TR using beads 42 delivered within a vessel V passing through or along the treatment region TR, rather than into the tissue of the treatment region TR surrounding the vessel V.

Similar to the previous method, a first member 120 is introduced into the vessel V and a second member 130 is introduced into the treatment region TR. The first member 120 is a catheter having a distal end 126 that may be advanced through the patient's vasculature, e.g., over a guidewire or other rail, until the distal end 126 is disposed within the vessel V. Manipulation of the distal end 126 may be monitored using external imaging, as described above. Once the distal end 126 is positioned adjacent the treatment region TR, beads 42 may be delivered from a source of beads (not shown) through a lumen 128 of the catheter 120 out the distal end 126 and into the vessel V.

The second member 130 may carry a magnet 132, e.g., an electromagnet similar to the embodiments described previously, that may be advanced into the treatment region TR until the magnet 132 is disposed adjacent the vessel V. The second member 130 may be a needle including a sharpened distal tip that be inserted directly into tissue and that may carry the magnet 132 on or adjacent the distal tip. Alternatively, the second member 130 may be a cannula or catheter that may be advanced through an introducer (not shown) previously inserted into the treatment region TR, similar to the methods described previously. The second member 130 may be introduced into the treatment region TR before or after the catheter 120 and/or magnetic beads 42 are delivered into the vessel V. The second member 130 may be advanced and/or manipulated to place the magnet 132 at a predetermined location relative to the vessel V. Alternatively, the second member may be a catheter introduced into another vessel (not shown) extending along or into the treatment region TR, similar to the methods described previously.

Once the second member 130 is positioned as desired within the treatment region TR, e.g., adjacent the vessel V, the magnet 132 may be activated to generate a magnetic field and cause the magnetic beads 42 to migrate within the vessel V. Preferably, the magnetic beads 42 move into contact with the wall of the vessel V that extends along the treatment region TR.

Energy, e.g., electrical energy, may be delivered into the treatment region TR, e.g., using one or more electrodes introduced into the treatment region TR, as described previously. Alternatively, the elongate member 130 that carries the magnet 132 may include one or more electrodes (not shown) that may be activated to deliver energy to the treatment region TR. The beads 42 along the wall of the vessel V may enhance heating of tissue adjacent the vessel V, thereby compensating for the heat sink effect that may otherwise occur due to the vessel V. In addition or alternatively, a source of energy may be activated to cause the beads 42 to heat the interior wall of the vessel, similar to the embodiments described above.

Thus, although several preferred embodiments have been shown and described, it would be apparent to those skilled in the art that many changes and modifications may be made thereunto without the departing from the scope of the invention, which is defined by the following claims and their equivalents.

What is claimed:

1. A system for treating tissue within a target tissue region, comprising:
    a source of beads;
    a first elongate member comprising a proximal end, a distal configured for introduction into a target tissue region, and a magnet carried by the distal end, the magnet configured for producing a magnetic field within the target tissue region to cause beads implanted within the target tissue region to migrate;
    a device for varying the magnetic field; and
    one or more electrodes for delivering energy to treat tissue within the target tissue region.

2. The system of claim 1, wherein the magnet comprises a coil.

3. The system of claim 2, wherein the device comprises a core wire coupled to a first end of the coil, the core wire moveable relative to a second end of the coil to thereby change a spacing between pitches of the coil.

4. The system of claim 1, wherein the magnet includes a first portion and a second portion that is electrically isolated from the first portion, the first portion configured to generate a first magnetic field when electrically activated, the second portion configured to generate a second magnetic field when electrically activated.

5. The system of claim 1, wherein the magnet is an electromagnet.

6. The system of claim 1, further comprising a second elongate member having a proximal end, a distal end configured for introduction into the target tissue region, and a lumen extending between the proximal and distal ends of the second elongate member for delivering beads from the source of beads to one or more outlets in the distal end of the second elongate member.

7. The system of claim 1, further comprising an electrical generator for delivering electrical energy to the one or more electrodes.

8. The system of claim 1, wherein the beads include conductive material for enhancing delivery of the electrical energy to the target tissue region.

9. A system for use with beads to treat tissue within a target tissue region, comprising:
    a first elongate member comprising a proximal end, a distal end configured for introduction into the target tissue region, and a coil carried by the distal end, the coil configured for producing a magnetic field within the target tissue region to cause beads implanted within the target tissue region to migrate; and
    a device for varying the magnetic field, wherein the device comprises a core wire coupled to a first end of the coil, the core wire moveable to a second end of the coil to thereby change a spacing between pitches of the coil.

10. The system of claim 9, further comprising a source of energy for delivering energy to treat tissue within the target tissue region.

11. A method for treating tissue within a target tissue region, comprising:
    introducing beads into a target tissue region;
    generating a magnetic field within the target tissue region; and
    varying the magnetic field to control the beads, wherein the magnetic field is determined based at least in part of one or both of a weight of the beads and a distance between a source of the magnetic field and the beads.

12. The method of claim 11, wherein the magnetic field is determined based at least in part on the weight of the beads.

13. The method of claim 11, wherein the magnetic field is determined based at least in part on a distance between the source of a magnetic field and the beads.

14. The method of claim 11, further comprising delivering energy to treat tissue within the target tissue region.

15. The method of claim 14, wherein the beads are caused to migrate towards a vessel located in the target tissue region so as to enhance delivery of energy to tissue adjacent the vessel.

16. The method of claim 14, wherein the energy to treat tissue is delivered by introducing one or more electrodes into the target tissue region, and coupling electrical energy to the one or more electrodes, the beads comprising conductive material for enhancing delivery of the electrical energy to the target tissue region.

17. A system for use with beads to treat tissue within a target tissue region, comprising:
  a first elongate member comprising a proximal end, a distal end configured for introduction into the target tissue region, and a magnet carried by the distal end, the magnet configured for producing a magnetic field within the target tissue region to cause beads implanted within the target tissue region to migrate, the magnet including a first portion and a second portion that is electrically isolated from the first portion; and
  a device for varying the magnetic field, wherein the first magnet portion is configured to generate a first magnetic field when electrically activated by the device, and the second magnet portion is configured to generate a second magnetic field when electrically activated by the device.

18. The system of claim 17, wherein the first and second magnet portions comprise electromagnets.

19. The system of claim 17, further comprising a second elongate member having a proximal end, a distal end configured for introduction into the target tissue region, and a lumen extending between the proximal and distal ends of the second elongate member for delivering the beads to one or more outlets in the distal end of the second elongate member.

20. The system of claim 17, further comprising a source of energy for delivering energy to treat tissue within the target tissue region.

21. The system of claim 20, wherein the source of energy comprises one or more electrodes.

22. The system of claim 21, further comprising an electrical generator coupled to the one or more electrodes for delivering electrical energy to the electrodes.

23. A method for treating tissue within a target tissue region, comprising:
  introducing beads into a target tissue region;
  generating a magnetic field within the target tissue region;
  varying the magnetic field to control the beads; and
  delivering energy to treat tissue within the target tissue region by introducing one or more electrodes into the target tissue region, and coupling electrical energy to the one or more electrodes, the beads comprising conductive material for enhancing delivery of the electrical energy to the target tissue region.

24. The method of claim 23, wherein the magnetic field is varied by changing a space between pitches of an electromagnetic coil.

25. The method of claim 23, wherein the magnetic field is generated by activating a plurality of magnets.

26. The method of claim 25, wherein the magnetic field is varied by changing a number of magnets that are activated.

27. The method of claim 23, wherein the beads are caused to migrate towards a vessel located in the target tissue region so as to enhance delivery of energy to tissue adjacent the vessel.

* * * * *